United States Patent [19]

Saunders et al.

[11] Patent Number: 4,599,307
[45] Date of Patent: Jul. 8, 1986

[54] METHOD FOR ELIMINATION OF SELECTED CELL POPULATIONS IN ANALYTIC CYTOLOGY

[75] Inventors: Alex M. Saunders, San Carlos; Chin-Hai Chang, Los Altos, both of Calif.

[73] Assignee: Becton, Dickinson and Company, Paramus, N.J.

[21] Appl. No.: 514,425

[22] Filed: Jul. 18, 1983

[51] Int. Cl.[4] .................... G01N 33/50; G01N 33/533
[52] U.S. Cl. .................................. 435/34; 250/461.2; 356/39; 436/63; 436/172; 436/519
[58] Field of Search ................. 436/63, 164, 172, 519, 436/807; 422/52, 68; 250/461.2; 356/39; 435/34

[56] References Cited

U.S. PATENT DOCUMENTS

| | | | |
|---|---|---|---|
| 3,826,364 | 7/1974 | Bonner | 209/3 |
| 3,883,247 | 5/1975 | Adams | 250/461.2 X |
| 3,916,205 | 10/1975 | Kleinerman | 250/461.2 |
| 4,243,318 | 1/1981 | Stohr | 250/461.2 X |
| 4,284,412 | 8/1981 | Hansen | 356/39 X |
| 4,336,029 | 6/1982 | Natale | 436/172 |

OTHER PUBLICATIONS

"Techniques in Immunocytochemistry", vol. 1, G. R. Bullock et al., eds., Chapt. Entitled 'Applications of Double-Label Immunofluorescence' by K. B. Pryzwansky, pp. 77-89, Academic Press, New York, 1982.

*Primary Examiner*—Sidney Marantz
*Attorney, Agent, or Firm*—James R. McBride

[57] ABSTRACT

A method for identifying subpopulations of cells of interest without interference from other cells. In the method, a sample of at least three (3) types of cells, including a first and second type of cell which form a subpopulation of cells of interest and a third type of cell which interferes with the identification of said subpopulation, is divided into at least two (2) aliquots. A first antibody which is specific for the third type of interfering cells but not for the subpopulation, is labeled with two (2) fluorochromes, each of the fluorochromes having distinct emission spectra. The labeled first antibody is then added to a first one of the sample aliquots so as to label the third type of cells with the first antibody. A first analysis is performed by analyzing each cell to determine the fluorescence emitted and to count the third type of cells so as to distinguish the third type of cells from the subpopulation. The information obtained from the first analysis is retained for subsequent use. The above steps are repeated for the subpopulation of cells of interest and a second analysis is obtained. The retained information from the first analysis is used to remove the effect of the third type of interfering cells and to provide a direct proportional analysis of the first and second types of cells in the subpopulation of cells of interest.

16 Claims, 6 Drawing Figures

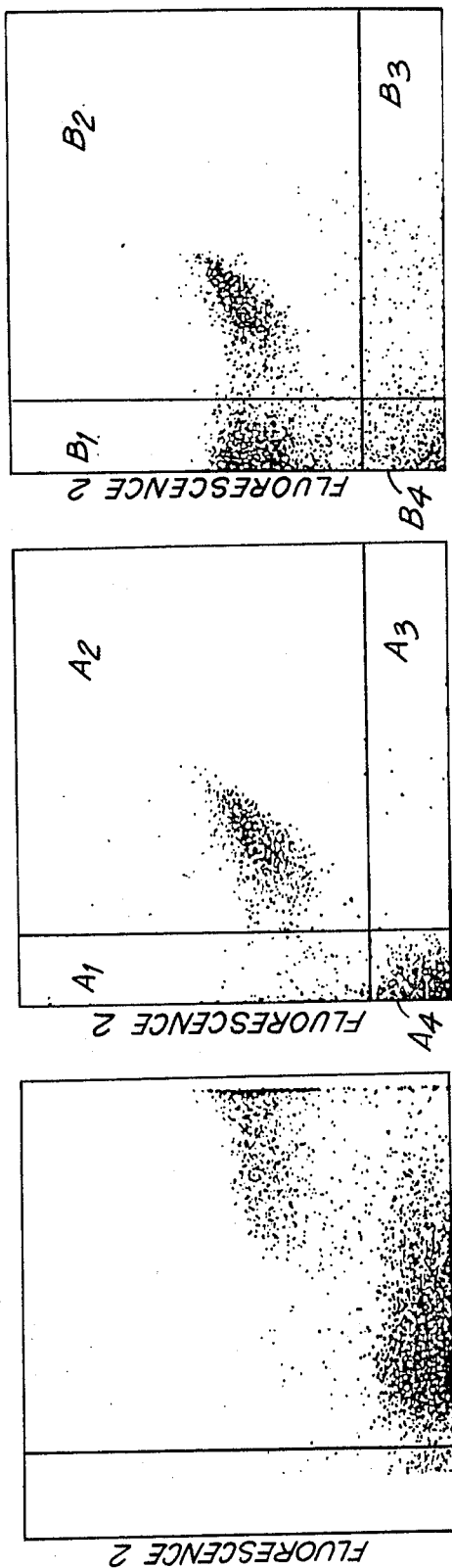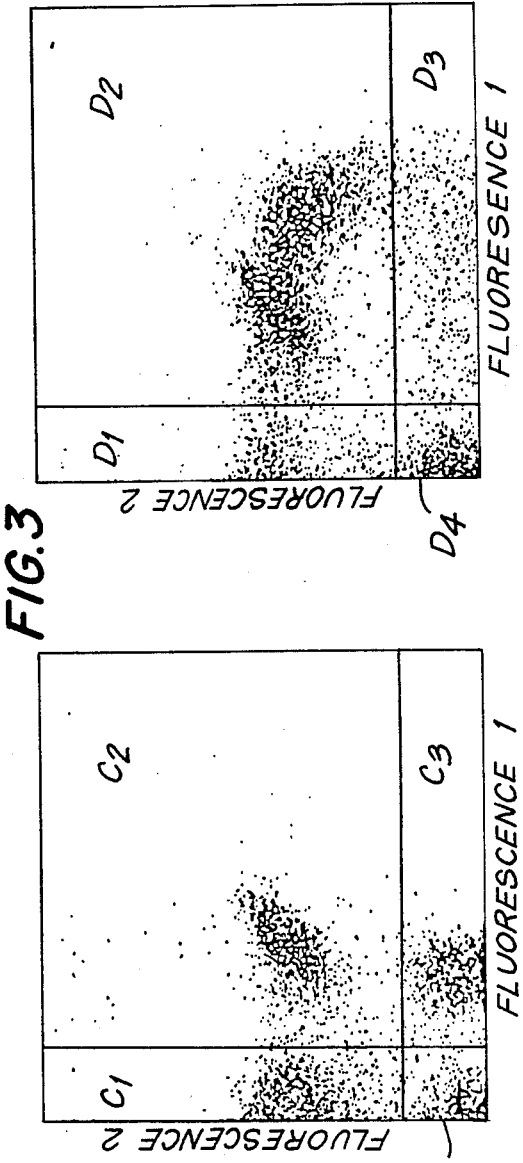

METHOD FOR ELIMINATION OF SELECTED CELL POPULATIONS IN ANALYTIC CYTOLOGY

BACKGROUND OF THE INVENTION

1. Field of the Invention

The present invention relates to a method and apparatus for distinguishing and identifying multiple subpopulations of particles in a sample without interference from other particles in the sample, and more particularly, relates to a method and apparatus for distinguishing and quantifying multiple subpopulations of cells of interest in a cell sample without interference from other cells having properties which would interfere with the quantifying of the cells of interest.

2. Description of the Prior Art

Presently known and available flow-through cytometers useful for detecting particles, cells and the like, commonly include two channels for the detection of one or more, usually two, subpopulations of cells in a mixture. For example, devices are known which include two fluorescence channels which can detect cells specifically labeled with two immunofluorescent agents associated with the respective fluorescence channels. In these known devices, a complete fluorescence channel including the electrical circuitry and fluorescence detector is used for each category of fluorochrome-treated cells to be detected in the mixture of cells in the sample being analyzed. Therefore, to detect multiple subpopulations of cells in a sample using flow-through cytometry, an equivalent number of fluorescence channels is used. A separate light source, such as a laser, is used to excite each different type of fluorochrome or immunofluorescent stain which has been tagged.

Analysis and quantifying of two different immunofluorescent stains in a single sample, utilizes two lasers providing excitation energy at significantly separated wave lengths or two fluorochromes which are activated by a single light source but which have different emission characteristics. Apparatus utilizing two lasers for analyzing an equivalent number of immunofluorescent stains are described in U.S. Pat. No. 3,826,364 and 4,284,412.

In the field of hematology in general, and in the specific field of immuno-hematology, it is desirable to determine the count of a variety of cells which circulate in the peripheral blood. Subclassification of cells is performed, and the count of the subclasses is of great interest in the evaluation of immune related disease, such as the recently recognized acquired immune deficiency syndrome (AIDS). In particular, the subclasses of the lymphocyte, a mononuclear type of white blood cell in blood, has become of great clinical significance.

There are many instances when it is desirable to be able to directly detect distinct multiple subpopulations of cells of interest from a sample, but where the sample has other cells having similar characteristics to the cells of interest interfere with such direct detection. For instance, in performing certain tests on blood, it may be desirable to detect or quantify the total population of lymphocytes cells in the blood sample and to determine the proportion of T-cells and B-cells as a percentage of the lymphocyte population. Lymphocyte cells, however, are mononuclear cells and other mononuclear cells, particularly monocytes, are present in the blood sample. Such other mononuclear cells interfere with a direct determination of T-cells and B-cells. Similarly, the detection and quantification of other different types of lymphocytes, such as the helper cell/suppressor cell subset of T-cells and the suppressor cell/natural killer cell subset of T-cells, may be desired. Monocytes would also interfere with such subset analysis. With this in mind, the present invention is directed to solving the aforementioned problems while satisfying the desired need for the direct determination of subpopulations of cells of interest from a sample mixture without interference from other cells having similar characteristics.

It would be desirable to provide an independent count of lymphocytes and of monocytes. Prior effects to provide such independent counts have concentrated on the fact that monocytes as a group are generally larger than lymphocytes. However, there is a large overlap of sizes between the lymphocytes and monocytes and such size difference methods have not been successful. In some diseases, small monocytes are abundantly present in peripheral blood and the size concept becomes completely invalid. Another means of identifying monocytes has depended on determination of an enzymatic reaction limited to monocytes. However, this means for classification and identification of monocytes is not compatible with the recognition of lymphocyte subsets.

Another aspect of the present invention is an apparatus for identifying multiple subpopulations of particles of interest in a sample containing other particles which would interfere with such identification. These particles have been selectively labeled with different marking agents having distinguishable, quantifiable characteristics capable of being stimulated. This apparatus comprises means for moving the labeled particles, substantially one at a time, in a flow path. Means is provided for stimulating the marking agents on the particles moving in the flow path. Such stimulating means is capable of stimulating the characteristics of two or more different marking agents on labeled particles. There are means for detecting the characteristics exhibited by the stimulated marking agents, means for distinguishing subpopulations of the particles relative to the detected, different quantifiable characteristics of the marking agents and means for retaining an analysis based on such detection and distinguishing means and applying the retained analysis to a subsequent or prior analysis.

SUMMARY OF THE INVENTION

In accordance with the principles of the present invention, a number of advantages and objectives are attained. Primarily, the present invention permits the detection and quantification of multiple subpopulations of particles or cells of interest in a sample without interferences from other particles or cells in the sample which are not of interest. Thus, cell subpopulations of interest can be determined by the passage of two prepared samples through a two laser flow cytometer. By selecting fluorescent labels which, though sufficiently separated in fluorescent wavelength to provide distinguishing characteristics, are close enough in spectral range to be excited by a single light source, dual color immunofluorescence results comparable to the two laser excitation mechanism can be achieved.

BRIEF DESCRIPTION OF THE DRAWINGS

FIG. 2 is a graphic representation of the results obtained by fluorescence and volume differentiation of a blood sample illustrating volume overlap of the interfering cells;

FIG. 3 is a graphic representation of the first analysis in accordance with the invention, and FIGS. 4–6 are a graphic representation of the detection and quantification of three subpopulations of lymphocytes in a sample determined by a passage through a flow cytometer in accordance with the principles of the present invention.

DETAILED DESCRIPTION

Figure 1:
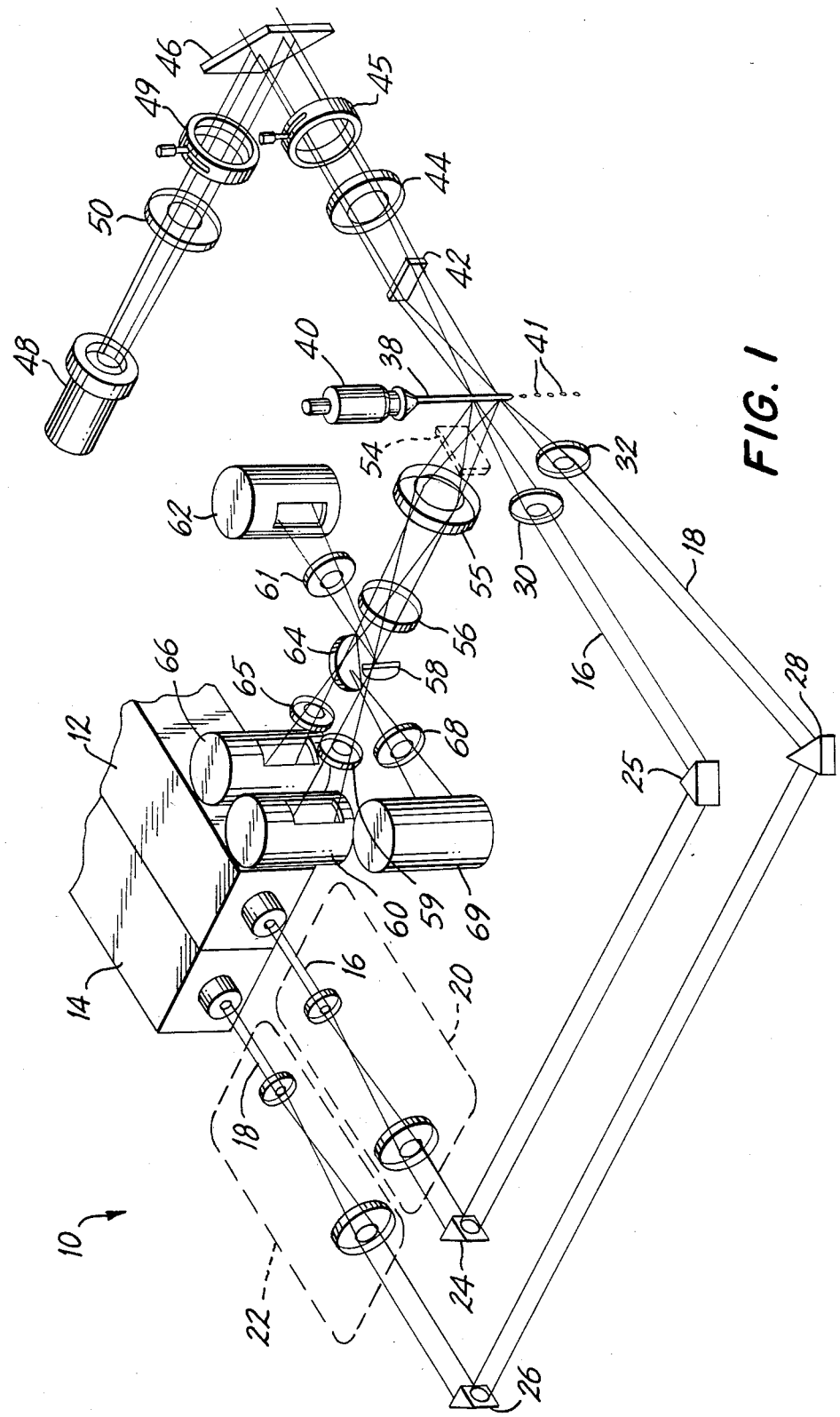
FIG. 1 is a schematic illustration of a preferred embodiment of the optical elements and light paths of a flow cytometry device particularly useful for determining fluorescence related to multiple subpopulations of particles and light scatter parameters of particles flowing in a flow path.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention is determined by the appended claims and their equivalents.

The present invention provides a method for identifying and excluding the effect of an interfering cell in the presence of other cells for which a more detailed study is required. In the method for distinguishing multiple subpopulations of cells of interest in a sample which contains other cells which would interfere with such identification, a sample of the subpopulations of cells of interest and the other interfering cells is provided and divided into at least two aliquots. A first analysis of the other cells which would interfere with the cells of interest is first made by labeling each of the other cells with a first marking agent and each of the other particles with a second marking agent, each of the marking agents having distinct emission spectra. The sample, containing the labeled other interfering cells is passed, substantially one cell at a time, successively through an area of detection to detect the emission characteristics of the two different marking agents on the other interfering cells. A first analysis is performed to determine the two types of fluorescence emitted and to count the other interfering cells and distinguish the other interfering cells from the subpopulation of cells of interest. The information obtained in the first analysis is then retained for future use.

In a second aliquot of the sample, one of the types of cells in the subpopulation of cells of interest is then labeled with the first marking agent used to label the other particles. Another type of cells of the subpopulation of cells of interest is then labeled with the second marking agent used to label the other cells. At the same time in the second aliquot of sample, the other type of interfering cells is again labeled with the two marking agents as described heretofore for the first analysis. The labeled cells of the second aliquot are then passed substantially one at a time through an area of detection to detect the characteristics of the labeled cells. A second analysis is then performed by analyzing each cell to determine the fluorescence emitted so as to distinguish each type of cell. The retained information from the first analysis is then applied to remove the effect of the other type of interfering cells and to provide a direct proportional analysis of the subpopulation of cells of interest an to exclude the effect of the other type of cells.

The marking agents are preferably fluorochromes which have an emission-spectra having sufficient wavelength separation to permit detection of two colors. One suitable pair of marking agents has been found to be phycoerythrin, a phycobiliprotein which emits fluorescense at 570 nm and fluorescein, which emits at a wavelength of 530 nm.

In FIG. 1 the optical and particle flow elements of a flow cytometry device 10 are illustrated. The optical and flow elements of FIG. 1 represent the major components of a flow cytometry instrument for flowing particles in a liquid stream, substantially one at a time, in order to analyze those particles for specific characteristics thereof. For example, the elements of the device of FIG. 1 may be included in a FACS (Trademark) fluorescence-activated sorter, manufactured and sold by the FACS Systems Division of Becton, Dickinson and Company, Sunnyvale, Calif. The FACS cell sorter analyzes and separates cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry devices, whether measuring light scatter, particle volume, fluorescence or any other optical parameters for the identification or quantification of subpopulations of particles in a sample.

As illustrated in FIG. 1, light energy is provided for the flow cytometry device by a suitable light source, 12 and 14, such as a laser. In the embodiment being described, two sources of light are provided in flow cytometry device 10 so that it is possible to detect and quantify a plurality of different types of particles having different fluorescence characteristics. It is understood, however, that the inclusion of two lasers in the embodiment illustrated in FIG. 1 is merely preferable and serves as an exemplary embodiment of employing more than one light energy source and analysis elements in the type of invention being described. Moreover, the elements of the present invention may be utilized just as satisfactorily if only one light source is employed in the flow cytometry apparatus. Also, it should be understood that a coherent light source, such as a laser, is not required. Other light sources, such as a mercury vapor lamp, are suitable and are preferred for some applications. Similarly, more than two light sources may be utilized, if feasible and practicable.

In the present invention, lasers 12 and 14 are selected to produce primary emissions of coherent light at specific wavelengths separated from each other in the spectral range. For example, laser 12 is preferably selected to operate in the blue/green spectral region whereby fluorochromes, which fluoresce when irradiated by optical stimulation of certain wavelengths, attached to particles passing through the light generated by laser 12 will become excited. One such laser useful for the present invention is an argon ion laser having a primary emission at 488 nanometers (nm). Laser 14 is preferably selected to operate at a different, separated wavelength from laser 12. Particles having fluorochromes thereon which fluoresce when irradiated by optical stimulation of the wavelength of laser 14 will become excited when these particles pass through the light generated by laser 14. The operation of laser 14 may cover the yellow/red region of the visible spectrum so as to be substantially separated in wavelength from the spectral region of laser 12. One such laser which satisfies this requirement is a Rhodamine 6-G dye laser which has a primary emission at 595 nm. It is desirable that the difference in wavelengths of the two lasers be substantial enough to be outside of the spectral range for exciting at least two fluorochromes with each laser. It has been found that a difference in wavelengths between the two lasers of 75 to 100 nm will permit the desirable result just described. Of course, the selection of the fluorochromes or other quantifiable marking agents must be compatible with the lasers which are used in the present invention so that up to two fluorochromes may be excited by the light energy provided by each laser.

Emerging from lasers 12 and 14, each beam 16 and 18, respectively, may pass through beam expanders schematically indicated by numerals 20 and 22 which enlarge each beam while retaining the parallel character thereof. As each beam emerges from the beam expander, which is preferable but not necessary for operation of the present invention, it normally must have its direction changed due to space requirements in the flow cytometry device. To this end, beam 16 is reflected through prisms 24 and 25, while beam 18 is reflected through prisms 26 and 28. All of these prisms may be made adjustable to properly align the beams during operation.

After beams 16 and 18 pass through the prisms, they are directed toward lenses 30 and 32 for focusing the beams onto the stream of particles. While lenses 30 and 32, if employed, are selected in accordance with the type of flow cytometry device being employed, these lenses may be selected in accordance with the description thereof in patent application, Ser. No. 361,672, filed in the U.S. Patent and Trademark Office on Mar. 25, 1982, and having a common assignee as the present application.

Once the laser beams pass through lenses 30 and 32, they are directed onto particle stream 38. A nozzle 40, incorporated within the flow cytometry device of the present invention facilitates the flowing of particles 41 within fluid stream 38. The utilization of a nozzle of this type is well-known and is described, for example, in U.S. Pat. No. 3,826,364. As seen more clearly in FIG. 1, laser beam 16 lies on the optical axis of a light-scatter channel and is used for scatter deteciton of particles. It is understood, however, that the light scatter features herein described are merely included to round out the features of a typical flow cytometry device which may rely upon light scatter to obtain information from particles passing through the light beams.

Thus, light beam 16 is the first light beam encountered by a particle flowing in stream 38 emerging from nozzle 40. Thereafter, beam 16 strikes the light-scatter obscuration bar 42 on the optical axis of the light-scatter channel. Scattered light, collected by the lens 44, passes through a first iris 45 which determines the maximum angle of scattered light collected. Following first iris 45 is a beam splitting mirror 46 which reflects a percentage of the incident light toward scatter detector 48, and transmits the remaining percentage of the incident light onto a light absorber (not shown). A second iris 49 functions as a field stop to restrict the source of scattered light to the point of intersection of laser beam 16 and stream 38. After passing through filter 50, the scattered light is detected in detector 48. This detector functions electrically to assess the size of the particles flowing in the fluid stream according to well-known techniques.

Laser beam 18 is also directed at flowing stream 38, but is vertically displaced from laser beam 16 along the vertical axis of the stream. Light from beam 18 scattered by a particle is picked up by the scatter-channel optics, but preferably blocked from detector 48 by the dielectric filter placed in the scatter channel.

With respect to the fluorescence channels, illumination provided by the different wavelength operation of the lasers is available for sequential excitation of fluorochromes having predetermined, separated emission spectra. Up to two fluorochromes having predetermined, separated emission spectra are excited by the excitation energy provided by the light energy of each laser. As seen in FIG. 1, the two independent laser beams intersect stream 38 at points vertically spaced so that a particle crosses laser beam 16 first and then laser beam 18. Accordingly, two pairs of optical signals may be generated by the particles passing through the light beams. These pairs of signals are preferably spaced in time by the time required for the particle to travel from the first beam intersection point to the second beam intersection point. This time spacing permits the pairs of signals to be separately analyzed giving signals proportional to the fluorescence emissions of the particles when excited at the two different excitation wavelength. Fluorescence signals emitted from the particles are directed around obscuration bar 54 which blocks refracted light from the separated beams. All fluorescence signals are focused by lens 55 preferably through a first filter 56 which permits light only at specific wavelengths to pass therethrough.

Fluorescence emitted by particles stimulated by light beam 16, after passing through filter 56, then encounters a dichroic mirror 58. The purpose of dichroic mirror 58 is to separate two different colors traveling along the fluorescence light path so that they can be analyzed separately. For example, dichroic mirror 58 would be selected to separate, for example, the different color wavelengths of particles excited by light beam 16 produced only by laser 12. For instance, wavelengths in the blue region would be transmitted through dichroic mirror 56 and then through a barrier filter 59 which is designed to transmit wavelengths of only one color region, in this instance blue. Blue light then enters a fluorescence detector 60.

Light encountering dichroic mirror in the green color region would be reflected by the dichroic mirror through a barrier filter 61 which transmits wavelengths of only one color region, in this case, green. A fluorescence detector 62 then receives this green light.

Light beam 18 also provides excitation energy at a single wavelength sufficient to excite up to two fluorochromes different from those excited by light beam 16. After the fluorescence emitted by the particles excited by light beam 18 passes through lens 55 and first filter 56, this light encounters another dichroic mirror 64. Similar to the description of dichroic mirror 58, the second dichroic mirror 64 is selected to separate the wavelengths of two different regions of the color spectrum. For example, both yellow and red signals may be generated as a result of the single excitation source provided by light beam 18 directed from laser 14. Wavelengths in the yellow region would be transmitted through dichroic mirror 64 and then through a barrier filter 65 which is designed to transmit wavelengths of only the yellow region. This light is then directed to a fluorescence detector 66. Wavelengths in the red region would be reflected by dichroic mirror through a barrier filter 68, whereupon this light enters fluorescence detector 69. Accordingly, it can be seen that light from two lasers, which can excite up to two different fluorochromes at the respective wavelengths of operation of each, allows the detection and quantification of multiple subpopulations of particles in a sample during a single pass of that sample in a flow cytometry device such as described.

Fluorescence detectors 60, 62, 66 and 69 are provided to preferably receive the four separated blue, green, yellow and red light paths, respectively. These fluorescence detectors may be low-noise photomultiplier tubes or the like which convert optical signals into electrical signals. These electrical signals are then fed electrically to be processed by the electronics (not shown) of the flow cytometry device for analysis or other purposes. Various displays, information presentation, accumulation or recordation may be provided in the flow cytometry device. In accordance with one embodiment of the invention a computer 71 is provided to retain and apply the results of the first analysis to a second analysis to provide the direct identification of a subpopulation of cells.

Operation of the present invention will now be described in conjunction with the following examples for illustrative purposes only. The examples exemplify, but do not limit the scope of the technique for detecting, distinguishing and/or quantifying multiple subpopulations of particles in a sample.

EXAMPLE I

In this example, two components, or subsets of lymphocytes, i.e., T cells and B cells, were directly determined as a percentage of total lymphocytes from a human blood source.

Equal proportions of anti-Leu M3, an antibody specific for a cell surface marker on monocytes, were labeled with phycoerythrin (PE) an immunofluorescent stain which, when excited, emits fluorescence of 570 nm, at or near the orange region of the color spectrum, and with fluorescein, by means of fluorescein isothiocyanate (FITC), an immunofluorescent stain which when excited emits fluorescence at a wavelength of 530 nm, placing it in the green region of the color spectrum. This reagent, a single antibody with two labels may also be prepared by first labeling the antibody with PE, purifying in the usual manner, and then labeling again with FITC, which step is followed by a final purification. In the present example the antibody is a monoclonal antibody against monocytes known as Leu M3, hence the twice labeled reagent is identified as double Leu M3 (DLM3).

Anticoagulated whole blood samples are prepared as follows. A mononuclear cell fraction is prepared by layering the whole blood sample carefully over density gradient solution, for example Ficoll-Paque (Trademark of Pharmacia Fine Chemicals), centrifugation of the layered sample at 400×G (gravity) for 30 to 40 minutes, and then isolating the layer of cells at the solution interface. This mononuclear cell fraction is washed repeatedly with a salt solution balanced and buffered to maintain viable cells (BSS). Washing is accomplished by first adding BBS, then centrifuging, then removing the supernatant, then resuspending cells in another portion of BSS.

After the final washing, the cells are again suspended, and enough BSS is added to provide approximately one million (1,000,000) cells per cubic centimeter (cc). At least two aliquots are made of the resuspended sample and these are further prepared before analysis.

For the first analysis an aliquot of 0.02 cc) 20 microliters) of suspended cells are mixed with 0.02 cc of DLM3 reagent. Both cells and reagent are maintained at 0° to 4° C. at the time of mixing and thereafter for $\frac{1}{2}$ hour. After $\frac{1}{2}$ hour of incubation, a further addition of 5 microliters of 1% formaldehyde is made and the sample is mixed, and again washed as indicated above. The first sample has now been prepared for analysis.

The first sample is passed through a flow cytometry apparatus, with radiation mainly at 488 nm. The optical signals provided by passing the cells, substantially one cell at a time, through the flow cytometry device were detected and used to provide the printout shown in FIG. 3.

As illustrated in FIG. 3, the results of this first analysis are isolation of two populations of cells. One population represents monocytes in that the anti-Leu M3 antibody has reacted with this population, an area labeled A2. Since this reagent is DLM3, the resultant monocyte population is labeled for both green fluorescence, FL1, and for red fluorescence, FL2. In contrast, the major proportion of cells is completely unstained, an area labeled A4. This is the lymphocyte population. There are less than 5% of cells labeled only in one or the other fluorescent color. It was determined, for example, that monocytes were 18.4 percent and lymphocytes, which are shown in area A4, were 78.8 percent of the mononuclear cells.

For the second analysis a second aliquot of prepared cell suspension is further processed with a second antibody reagent. This second antibody reagent is composed of monoclonal antibodies against all T cells, being a mixture of anti-Leu 2a and anti-Leu 3a labeled with PE, in addition to a polyclonal antibody against surface immunoglobulin anti-IgM and anti-IgD labeled with FITC, plus the anti monocyte reagent DLM3 previously described. Incubation, fixing and washing steps for the second aliquot are identical to the steps by which the first aliquot are prepared. The second aliquot sample has now been prepared for analysis and is analyzed by passing the sample through a flow cytometry device to provide the analysis plot shown in FIG. 4.

As illustrated in FIG. 4, the monocyte population is again seen in the region where both red and green fluorescence are positive, the area marked B2. Occasional cells in addition to monocytes also appear in this B2 area. These are cells which have been labeled by both T cell reagent and B cell reagent. The number of these T+B+ cells may be determined by subtracting the number of monocytes determined in the first aliquot, area A2, from the total number of cells counted in area B2 of the second aliquot. As can be further seen in FIG. 4, there are cells present in region B1, representing cells labeled only as T cells and there are cells present in region B3 representing cells labeled only as B cells.

Table 1 presents the numerical results obtained from performing the measurement, classification and counting of the first aliquot and the second aliquot of the same mononuclear cell sample.

TABLE 1

| Region | Aliquot A Total | Aliquot A % | Aliquot B Total | Aliquot B % | Interact Aliquot, A & B Total | Interact Aliquot, A & B % |
|---|---|---|---|---|---|---|
| 1 | 228 | 2.3 | 6665 | 68.2 | 6665 | 77.5 |
| 2 | 1182 | 12.1 | 1359 | 13.9 | 176 | 2.0 |
| 3 | 18 | 0.2 | 251 | 2.6 | 251 | 2.9 |
| 4 | 8309 | 85.3 | 1502 | 15.4 | 1502 | 17.5 |
| Total | 9737 | | 9777 | | 8594 | |

The third column in Table 1 represents the interaction of results in Aliquot A with Aliquot B in the following way. Monocytes identified in region A2 are subtracted from the total cell count of 9737 cells in Aliquot B to give 8555 which is the total number of lymphocytes. This number 8555 becomes the denominator of the calculated results. Percent of monocytes of A2 are also subtracted from region B2 to give (1359−1183) or 176 non monocyte cells which had both T cell and B cell label. Percentage of each cell type is recalculated, based on the denominator (interactive total) of 8594. Thus the percentage of T cells is 77.5 and the percentage of B cells is 2.9 when represented as a proportion of lymphocytes only. Without this interactive calculation, the results would have been 68.2% T cells and 2.6% B cells. The difference is indicative of potential error of current systems when presence of monocytes is ignored.

As a further example, a third aliquot of the prepared mononuclear cells is mixed with a third reagent. The third reagent is composed of a solution of antibody against suppressor cell surface marker anti-Leu 2a labeled with PE and antibody against helper cell surface marker anti-Leu 3a labeled with FITC, in addition to DLM3 as used in the first aliquot. Mixing, incubation, fixing, washing and counting are performed as already described. The results are presented in FIG. 5 and are summarized in Table 2.

As yet a further example, a fourth aliquot of the prepared mononuclear cells is mixed with a fourth reagent. The fourth reagent is composed of a solution of anti-Leu 2a labeled with PE and a monoclonal antibody against Natural Killer cells surface marker, anti-Leu 7, labeled with FITC, in addition to DLM3. Mixing, incubation, fixing, washing and counting are performed as already described. Results are presented in FIG. 6 and Table 2.

TABLE 2

| Region | Aliquot C Total | Aliquot C % | Interacted Aliquot A & C Total | Interacted Aliquot A & C % |
|---|---|---|---|---|
| 1 | 3418 | 35.2 | 3418 | 40.1 |
| 2 | 1522 | 15.7 | 348 | 4.1 |
| 3 | 2865 | 29.5 | 2865 | 33.6 |
| 4 | 1896 | 19.5 | 1896 | 22.2 |
| Total | 9701 | | 8527 | |

| Region | Aliquote D Total | Aliquote D % | Interacted Aliquote A & D Total | Interacted Aliquote A & D % |
|---|---|---|---|---|
| 1 | 1296 | 13.5 | 1296 | 15.3 |
| 2 | 3615 | 37.6 | 2451 | 29 |
| 3 | 1128 | 11.7 | 1128 | 13.3 |
| 4 | 3584 | 37.2 | 3584 | 42.3 |
| Total | 9623 | | 8459 | |

By further calculation, it can be seen that the total fraction of suppressor cells is 44.2% of which 4.1% are also labeled as helper cells, or again the total fraction of suppressor cells is 44.3% of which 29% are Natural Killer cells. The difference between 44.2% and 44.3% is within the reproducibility of the method and the error produced by rounding of quotients in the five interacted or compared results. In the example shown, it is apparent that cells may be labeled with both anti-Leu 2a and anti-Leu 7.

Regions B4, C4 and D4 contain unlabeled lymphocytes which are considered as part of the total population of lymphocytes.

EXAMPLE 2

In this example two types of interfering cell types are eliminated from the count. Separate identity of the two types of interfering cells can be maintained while performing a classification of the subsets of interest.

The starting sample in this example is whole blood, anticoagulated with heparin, although other types of anticoagulant such as EDTA or Acid Citrate Dextrose are also satisfactory. The liquid sample is divided into at least two aliquots.

A reagent for the first aliquot contains antibody against Leu M3, (labeled with PE) and also contains antibody against Leu M1 (labeled with FITC), in a saline solution buffered to maintain pH and osmolality of solution close to that of blood. Leu M1 and Leu M3 are both cell surface markers on monocytes. Leu M1 is a cell surface marker on granulocytes and monocytes. This reagent is incubated with the first aliquot of whole blood at 4° C. for a period of 30 minutes. Following incubation, the red blood cell (RBC) component of the whole blood is eliminated, for example, by destroying the osmotic relationship between the inside and outside of each cell. The exact method of hemolysis is not important to this example as long as the white blood cells (WBC) are properly preserved. In one such example the RBC's are lysed using distilled water, while a small amount of formaldehyde in the water serves to preserve the WBC which contain both cells of interest (i.e., lymphocytes) and two types of interfering cells (i.e., monocytes and granulocytes).

The first aliquot is passed through a two color flow cytometry device as herein previously described, and individual cells are assigned to one of four compartments according to their fluorescence in two, one or none of the colors being measured. Therefore, in this aliquot the two interfering cell types are separately identified because granulocytes are labeled with anti-Leu M1 only and therefore fluoresce green only, while monocytes are labeled with both anti-Leu M1 and with anti-Leu M3 and therefore fluoresce both red and green. Cells assigned to the four compartments are separately counted and the count is retained.

A second aliquot of whole blood is similarly treated, lysed and counted. However, in this second aliquot the reagent contains in addition to anti-Leu M1 (FITC) and anti-Leu M3 (PE), an antibody against Leu 2a labeled with PE which identifies the suppressor subset of T cells and an antibody against Leu 7 labeled with FITC which identifies natural killer cells. Classification of cells processed in the flow cytometer after this incubation indicate suppressor cells fluorescing red only, monocytes and cells having both suppressor and natural killer markers fluoresce both red and green, while granulocytes and natural killer cells fluoresce green only.

By interacting the count of the first aliquot with the count of the second aliquot, interference from both granulocytes and monocytes is eliminated while suppressor cells, natural killer cells and cells possessing both suppressor and natural killer markers may be calculated as a percent of lymphocytes only.

EXAMPLE 3

In each example above, the first aliquot is used as the one for interactive counting.

In the following example, three different colored fluorochromes are used and are subsequently measured separately. In the first aliquot, monocytes are stained with Leu M3 (PE) and with Leu M1 (FITC) while granulocytes are stained with Leu M1 (FITC).

Measurement and classification of this first aliquot presents monocytes as red and green fluorescent while granulocytes are only green fluorescent.

In a second aliquot, the reagent contains, in addition to anti-Leu M3 (PE) and anti-Leu M1 (FITC), antibody against Leu 11 which is another marker identifying natural killer cells and also granulocytes. Anti-Leu 11 is labeled with Allophycocyanine, a fluorochrome which fluoresces a deep red when excited at 543 nm. In addition, the reagent for this second aliquot contains the anti-Leu 2a (PE) and anti-Leu 7 (FITC). After passing through a three color flow cytometer, it is possible to classify cells into eight compartments, one each of treble color and of no color, three of single color and three of double color.

In this example monocytes are red and green, granulocytes are deep red and green, suppressor cells are red only, natural killer cells identified by anti-Leu 7 only are green only, natural killer cells identified by anti-Leu 11 only are deep red only, while suppressor cells which are also marked with Leu 7 are red and green, and natural killer cells which are marked with Leu 7 and Leu 11 are green and deep red.

In addition, cells which would have all 3 markers—Leu 2, Leu 7 and Leu 11—would fluoresce in all three colors. These cells are not known at this time. By interaction of results from the first aliquot and the second aliquot it is possible to calculate all Leu 2+ lymphocytes, all Leu 7+ lymphocytes and all Leu 11+ lymphocytes as a percentage of lymphocytes and also to calculate the percentage of lymphocytes which have any combination of suppressor or natural killer markers.

What is claimed is:

1. A method for identifying subpopulation of cells of interest without interference from other cells comprising
   a. providing a sample of at least three types of cells including at least a first and second type of cell which form a subpopulation of cells of interest and at least a third type of cell which interferes with the identification of said subpopulation,
   b. dividing said sample into at least two aliquots,
   c. labelling a first antibody which is specific for said third type of cells but not for said subpopulation with at least two fluorochromes, each of said fluorochromes having distinct emission spectra,
   d. forming a mixture of said differently labelled first antibody with a first one of said sample aliquots so as to label said third type of cells with said first antibody,
   e. providing excitation energy to said first sample aliquot by cytometry techniques to excite each type of said fluorochromes,
   f. performing a first analysis by analyzing each cell to determine the fluorescence emitted and to count said third type of cells and distinguish said third type of cells from said subpopulation,
   g. retaining the information provided by said first analysis,
   h. labelling a second antibody which is specific for said first type of cells of said subpopulation with at least one of said fluorochromes used to label said first antibody,
   i. labelling a third antibody which is specific for said second type of cells of said subpopulation with at least one of the other of said fluorochromes used to label said first antibody,
   j. forming a mixture of said differently labelled first antibody, said labelled second antibody and said labelled third antibody with another of same sample aliquots so as to label said first, second and third type of cells with the antibody specific for the respective type of cell,
   k. providing excitation energy to said second sample aliquot by cytometry techniques to excite each type of said fluorochromes,
   l. performing a second analysis by analyzing each cell to determine the fluorescence emitted and to count said first, second and third types of cells and to distinguish each type of cell,
   m. applying the retained information of said first analysis to remove the effect of said third type of cells and to provide a direct proportional analysis of said first and said second type of said subpopulation of cells of interest.

2. A method in accordance with claim 1 wherein said subpopulation of cells of interest include T cells and B cells.

3. A method in accordance with claim 1 wherein said subpopulation of cells include helper cells and suppressor cells.

4. A method in accordance with claim 1 wherein said subpopulation of cells include suppressor cells and natural killer cells.

5. A method in accordance with claim 1 wherein said third type of interfering subpopulation cells is monocytes.

6. A method in accordance with claim 2 wherein said third type of interfering cells is monocytes.

7. A method in accordance with claim 3 wherein said third type of interfering cells is monocytes.

8. A method in accordance with claim 4 wherein said third type of interfering cells is monoctyes.

9. A method in accordance with claim 1 wherein said sample is a peripheral blood sample.

10. A method in accordance with claim 9 wherein said peripheral blood sample is treated to recover a mononuclear cell fraction prior to proceeding with Step b through Step m.

11. A method in accordance with claim 1 wherein said information retained from said first analysis is stored in a computer.

12. A method in accordance with claim 11 wherein the information obtained by performing said second analysis is stored in said computer and the retained information of said first analysis is applied by said computer to the information obtained from said second analysis to provide a direct proportional analysis of said first and said second type of cells from said subpopulation of cells of interest.

13. A method in accordance with claim 1 wherein said cytometry technique is flow cytometry.

14. A method in accordance with claim 1 wherein a further component of said subpopulation of cells of interest is identified by being labeled with both said second antibody and said third antibody.

15. A method in accordance with claim 14 wherein said further component is separately accounted for during said application of said retained information of said first analysis.

16. A method in accordance with claim 1 wherein more than one type of interfering cells is identified and accounted for during said second analysis.

* * * * *